United States Patent
Jerasi (10) Patent No.: US 11,759,587 B2
(45) Date of Patent: Sep. 19, 2023

(54) APPARATUS FOR ENHANCED NOSTRIL BREATHING

(71) Applicant: Meir Jerasi, Ramat Gan (IL)

(72) Inventor: Meir Jerasi, Ramat Gan (IL)

( * ) Notice: Subject to any disclaimer, the term of this patent is extended or adjusted under 35 U.S.C. 154(b) by 919 days.

(21) Appl. No.: 16/631,183

(22) PCT Filed: May 8, 2018

(86) PCT No.: PCT/IL2018/050498
§ 371 (c)(1),
(2) Date: Jan. 15, 2020

(87) PCT Pub. No.: WO2019/043681
PCT Pub. Date: Mar. 7, 2019

(65) Prior Publication Data
US 2020/0215281 A1    Jul. 9, 2020

(30) Foreign Application Priority Data

Sep. 4, 2017  (IL) .......................................... 254328

(51) Int. Cl.
*A61M 16/00*  (2006.01)
(52) U.S. Cl.
CPC . *A61M 16/0066* (2013.01); *A61M 2202/0007* (2013.01); *A61M 2205/103* (2013.01); *A61M 2210/0618* (2013.01)
(58) Field of Classification Search
CPC ...... A61M 16/0066; A61M 2202/0007; A61M 2205/103; A61M 2210/0618
See application file for complete search history.

(56) References Cited

U.S. PATENT DOCUMENTS

| | | | |
|---|---|---|---|
| 2,237,954 A | 4/1941 | Wilson | |
| 3,747,597 A | 7/1973 | Olivera | |
| 4,221,217 A | 9/1980 | Amezcua | |
| 4,267,831 A * | 5/1981 | Aguilar | A62B 23/06 128/203.14 |
| 4,653,494 A * | 3/1987 | Ruderian | A61M 16/108 128/203.22 |
| 6,386,197 B1 | 5/2002 | Miller | |
| 6,684,879 B1 | 2/2004 | Coffee et al. | |
| 6,715,485 B1 | 4/2004 | Djupesland | |
| 7,100,605 B2 * | 9/2006 | Opitz | A61M 15/02 128/202.13 |
| 7,740,643 B2 | 6/2010 | Maryanka | |
| 10,926,051 B2 * | 2/2021 | Collazo | A61M 16/0666 |

FOREIGN PATENT DOCUMENTS

| | | |
|---|---|---|
| CN | 01518677 A | 9/2009 |
| CN | 102872511 A | 1/2013 |
| CN | 205516070 U | 8/2016 |
| RU | 2441676 C1 | 2/2012 |
| WO | 20070023607 | 3/2007 |
| WO | WO-2017002051 A1 * | 1/2017 |

* cited by examiner

*Primary Examiner* — Steven O Douglas (57) ABSTRACT

An air inhalation device for insertion within the nostrils, comprising: at least one hollow frusto-conical tube member having an air passageway; a fan; a motor; and a power source; wherein the said frusto-conical tube has a forward end which tapers to form a rearward end, and is fitted with a power driven fan for enhancing the inhalation and exhalation of air.

5 Claims, 8 Drawing Sheets

APPARATUS FOR ENHANCED NOSTRIL BREATHING

RELATED APPLICATIONS

This application is a National Phase of PCT Patent Application No. PCT/IL2018/050498 having International filing date of 8 May 2018, which claims the benefit of priority of Israeli Patent Application No. 254328, filed 4 Sep. 2017. The contents of the above applications are all incorporated herein by reference.

FIELD OF THE INVENTION

This invention relates generally to the field of a nostril breathing enhancing apparatus, more specifically to a fan ventilation breathing enhancing apparatus, which can be fitted onto nostrils that not only allows dilation of the nostril but also acts as a filtering device to enable enhancement in the volume of inhaled air.

BACKGROUND OF THE INVENTION

The inhaled air often contains many particles and contaminants considered to be the prime sources of numerous allergic reactions and health problems. As a result, millions of people suffer from nasal obstructions or physiological conditions like narrowing of the nasal valve, allergic reactions, enlarged adenoid tissue, swollen nasal mucosa thus making nasal breathing difficult, uncomfortable, or nearly impossible. Decongestants allow temporary reduction in swellings and ease out breathing. However, in the long run, these may cause an increase in swelling thus rendering nasal breathing difficult. People seeking a non-drug related solution to this problem can opt for mechanical device or appliance that can take care of the mentioned deficiencies of the decongestants. The present invention relates to a novel device that allows the dual function of dilating the nostril apart from filtering the inhaled air. The fitting of the device in the nostril allows portability of the device.

There is currently no prior art that addresses all of these issues. However, some of the prior arts have attempted to deal with these issues by applying devices to both the outside of the nose and by inserting devices into the nasal cavities. The first two inventions talks about nasal dilation devices while the others talks of ways to filter.

For example, U.S. Pat. No. 7,740,643 (B2) discloses an adjustable nasal cavity dilation device with a first deformable body having a shape corresponding to the nasal cavity. Top and bottom frame ends of the body are interconnected by a flexible wall structure that undergoes deformation in response to movement of one frame end relative to the other. A releasable holding member includes a ring that engages the bottom frame end and an upstanding central member that engages the top frame end. The ring and the upstanding central member are coupled by a plurality of radial arms. The flexible wall structure is deformed and effective for urging against nasal cavity walls to increase air flow through the nasal passage when the top and bottom frame ends are maintained in a holding condition by the ring and the upstanding central member. The ring and radial arms define openings that permit passage of air into and out of the nasal cavity through the releasable holding member.

U.S. Pat. No. 6,386,197 describes a nasal passageway opening device including a body defining an airflow channel there through for insertion in the nasal passageway. The body may be conical, and may include a plurality of external protrusions to increase frictional resistance with the nasal passageway. The body may be solid, or hollow to incorporate a medicament therein, such as a mentholated gel. If the body is hollow, the interior surface may include a plurality of apertures for release of the medicament. The device is positioned within the nasal passage a sufficient distance so that it is hidden from view, thus illuminating the need for unsightly external nasal strips or topical applications of odiferous mentholated gels.

As to some of the patents that discuss filtering of polluted air or other gases through nostril fitted devices, it is pertinent to browse RU2441676 that refers to a device comprising of two housings that may be located in the sinus, each having an inport and an exhaust port, whereas the inner housing surface is covered in a layer of a sticky substance, equipped with an airflow conversion device fixed in the housing cavity by an axis, by a fixing device connecting the two housing parts from the exhaust ports. The housing provides a filter screen located from the exhaust port's side. describes a device comprises a two housings that may be located in the sinus, each having an inport and an exhaust port, whereas the inner housing surface is covered in a layer of a sticky substance, equipped with an airflow conversion device fixed in the housing cavity. The composite individual respiratory protection devices can be used on human and on animal patients in order to protect them from harmful environmental factors.

U.S. Pat. No. 4,221,217 describes an article for holding one or more replaceable elements in the nasal passages of a human being for affecting gases passing through such elements that includes a loop-shaped clip having a holder for such elements, preferably at one or both ends of the loop.

U.S. Pat. No. 3,747,597 refers to a nasal filter, characterized by the fact of being formed by a body having two hollow projections which can be located in the nasal fossae and which are provided with respective frusto-conical chambers the major bases of which are closed and provided with a plurality of holes, the minor bases being open; said chambers having two corresponding spheroidal hollow members the laminiform facings of which are perforated and their diameters being somewhat larger than the inside diameters of the minor bases and considerably smaller than the diameters of the major bases of said projections, said spheroid members being filled with filtering substances and said projections being provided with retaining temples to be applied to the outer part of the nasal fossae.

Each of the above invention talks about nasal filtering process. Despite filtering of inhaled air what is actually found is the reduced volume of inhaled air thus negating the positive impact of pure filtered air by the patient.

SUMMARY OF THE INVENTION

It is an object of the present invention to provide a novel dilator-filter apparatus that improves both nasal breathing and filtration more specifically to fan ventilation breathing enhancing apparatus thereby promoting better health.

Another object of the present invention is to develop a novel breathing enhancing apparatus that could be fitted in a nostril with a power driven fan that enhance the amount of air inhaled.

It is therefore another object of the invention to develop a novel breathing enhancing apparatus that reduces nasal air flow resistance and allows greater volume of pure and clean inhaled nasal intake and at the same time lesser oral intake of impure air intake, thus, improving sleep.

Another object of the present invention is to develop a novel breathing enhancing apparatus that have an outer body with an air entrance opening in the bottom and air flow exit on the top and is equipped with a small venting fan, with a motor and a rechargeable power source.

Still another object of the invention is to incorporate the motor in on of at least three different locations of the novel breathing enhancing apparatus. In some, it may be placed at the center of the fan, while in some others it can be placed in the exterior ring around the fan or just under the fan surrounded by an axial perimeter.

Another object of the invention is the incorporation of an embodiment in the novel breathing enhancing apparatus that allows positioning of the power button in the connection member that connects the two devices with the two nostrils. Furthermore, the power button has requisite provision to be placed on the edge of the outer body of the device and can be operated once the apparatus is fitted on the nostril.

Still another object of the invention is the incorporation of an embodiment as of a micro-switch that powers the fan upon inhaling air in two directions in accordance with the inhaled or exhaled air volume requirements.

Still another object of the invention is the incorporation of an optional embodiment in the novel breathing enhancing apparatus that comprises of a miniature container of preferred fragrance to allow good smell of the inhaled air.

It is therefore another object of the invention to incorporate an embodiment in the novel breathing enhancing apparatus in the form of a filter to prevent against certain air-transmitted allergies or of polluted air situations.

REFERENCE NUMERALS 100 hub with fan blades
10 blades
12 central hub
14 motor
16 16' frusto-conical tubes
18 connecting member
20 20' forward end
22 22' rearward end
24 power source
102 Nose
26 fragrance container
28 power switch
30 air filter
32 circular frame
34 central axis

DETAILED DESCRIPTION OF THE PREFERRED EMBODIMENTS

Referring to the drawings, an air inhalation device is provided for insertion into nostrils, the nostrils having interior wall surfaces, comprising: a pair of generally hollow frusto-conical tube members, each tube member having an air passageway and an exterior surface, each tube member being designed to be received by a nostril and a connection member for connecting the tube members.

An air inhalation device is provided for insertion into nostrils, comprising: a pair of generally hollow frusto-conical tube members, each tube member having an air passageway, a forward end, and a rearward end, each tube member being designed to be received by a nostril, the forward end of each tube member being tapered inwardly in the rearward direction extending to form the rearward end of each tube member; and a connection member for connecting the tube members.

Figure 3:
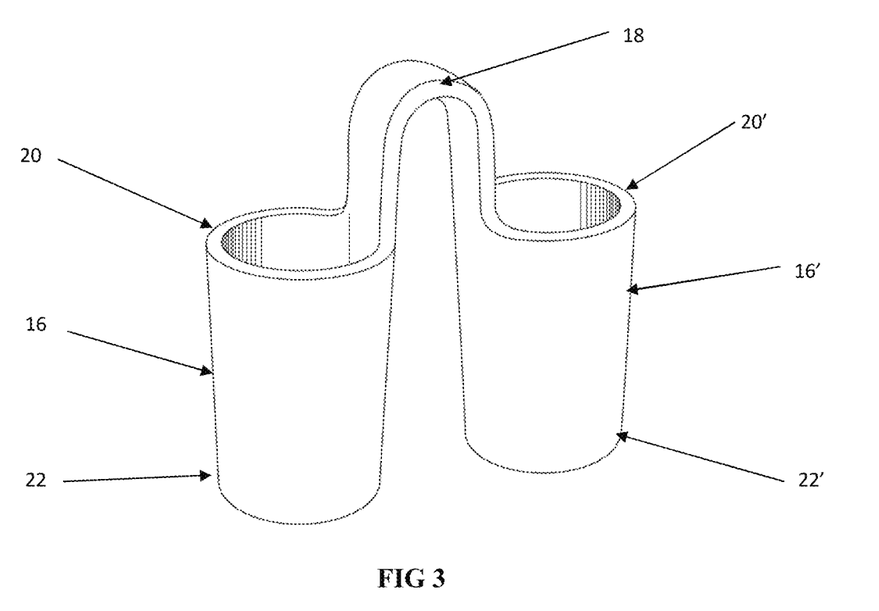
FIG. 3 illustrates a pair of frusto-conical tubes connected to a connection member of the present invention.

Referring now to FIG. 3, a pair of generally hollow frusto-conical tubes (16), (16'0 is provided. The left tube (16) and the right tube (16'), each have an exterior surface and an interior surface. The tubes (16), (16') are sized to be insertable within a typical nostril (102).

Each frusto-conical tube has a forward end (20), (20') and a rearward end (22), (22'). Each forward end (20), (20') tapers inwardly, as shown in FIG. 3 to form a frusto-conical tube of the present invention.

Figure 1:
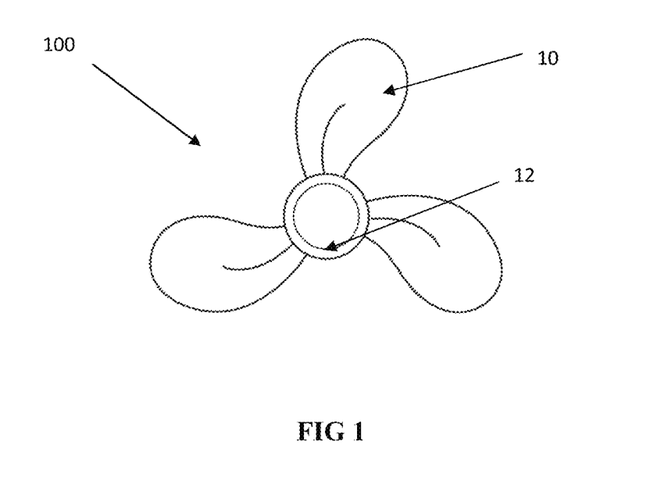
FIG. 1 is a top view of the vent of the fan of the present invention.
Figure 2:
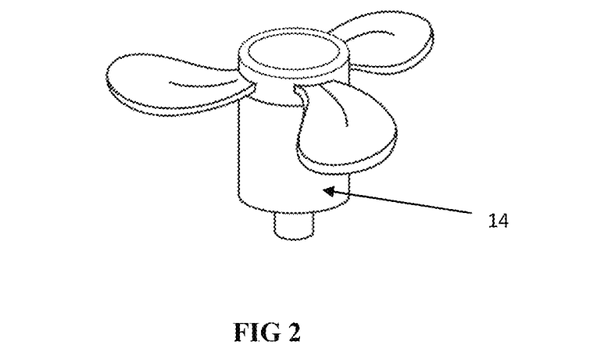
FIG. 2 is a side view of the vent of the fan with the motor of the device of the present invention.
Figure 12:
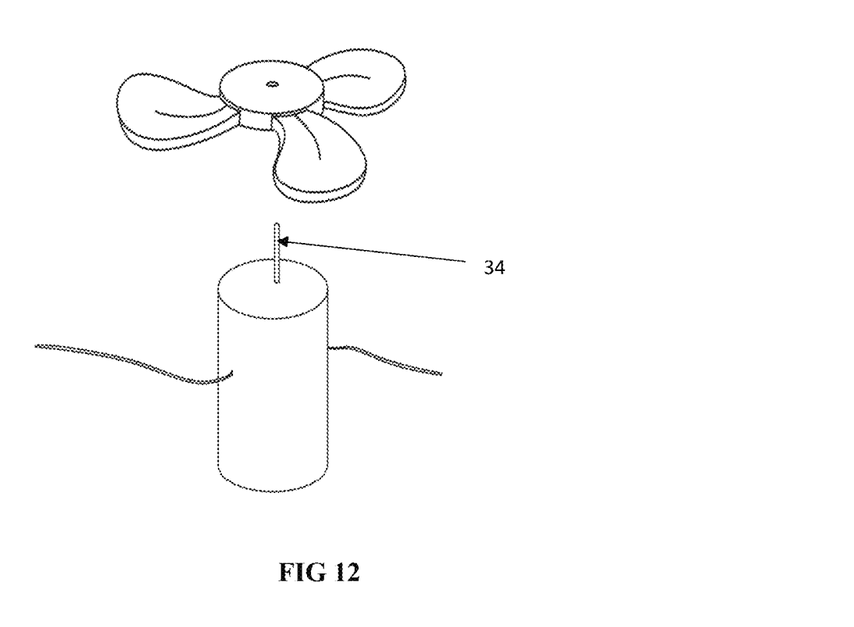
FIG. 12 illustrates the hub of the fan and the motor with a central axis.

As shown in FIGS. 1-2 and 12, a connection member (18) connects the tubes (16), (16'). The connection member (18) is of sufficient length to allow both tubes (16), (16') to be inserted fully in the nostrils (102).

Figure 4:
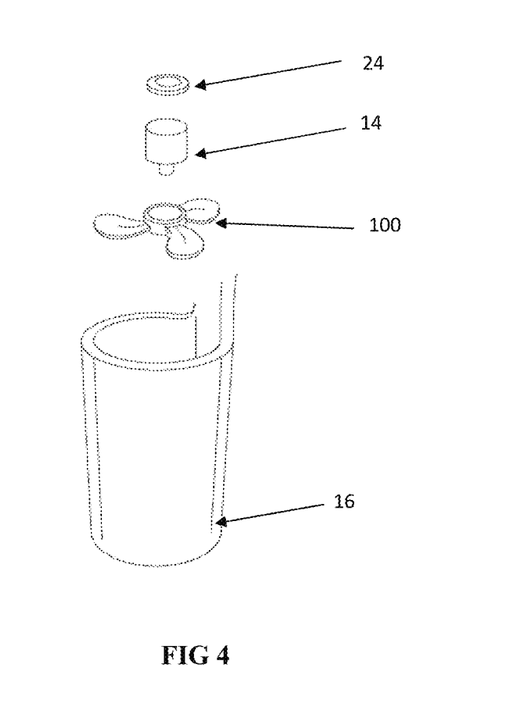
FIG. 4 illustrates a frusto-conical tube and segregated fan, motor and power source of the present invention.

Referring to FIGS. 3 and 4, each of the frusto-conical tubes houses a small fan provided with three blades. The fan comprises a motor which operates with a rechargeable battery also housed within the device.

Referring again to FIGS. 1 and 2, a vent fan along with its motor (14) is depicted. The fan blades (10) are affixed at the central hub (12) that is shaped like a flat disc.

Figure 5:
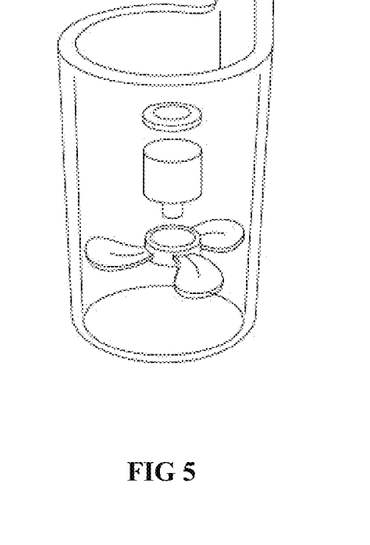
FIG. 5 illustrates a frusto-conical tube accommodating the segregated fan, motor and power source of the present invention.
Figure 6:
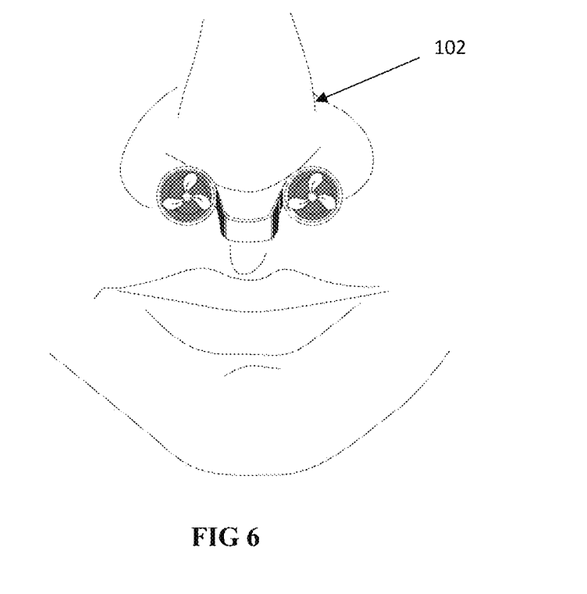
FIG. 6 illustrates the nasal ventilating device in both the nostrils with the connecting member of the present invention.
Figure 7:
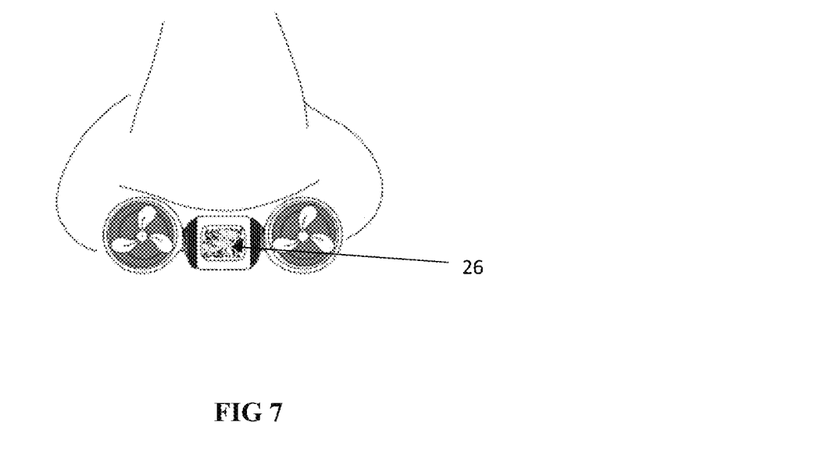
FIG. 7 illustrates the nasal ventilating device in both the nostrils with the connecting member accommodating a fragrance concentrate of the present invention.
Figure 8:
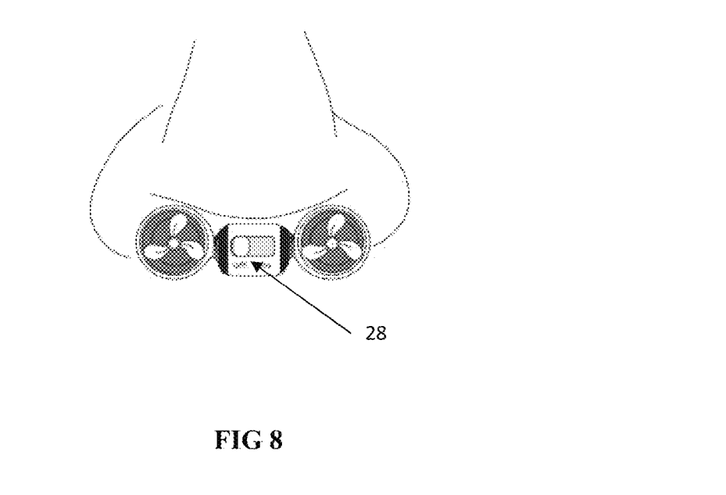
FIG. 8 illustrates the nasal ventilating device in both the nostrils with the connecting member accommodating a power switch of the present invention.

Referring to FIGS. 4-5, one of the hollow frusto-conical tube is depicted, housing the fan comprising a disc base, the hub (12) and a plurality of blades or vanes (10) arranged around the said hub (12).

In the above figure, the motor (14), is also depicted which is received by the hub of fan. The said hub of the fan comprises of receiving means (not shown) for receiving the said motor (14) of the fan assembly.

In this embodiment, the powering source or the battery (24) for the apparatus is in the form of circular flat disc, wherein the said motor (14) is connected with the said battery (24) as referred to in FIG. 12.

In an embodiment of the present invention, the said air inhalation device can be provided both at the said forward end (20, 20') and the said rearward end (22, 22') of the said hollow frusto-conical tubes (16,16'). The said blades (10) of the said air inhalation device are operable by a micro switch (28) accommodated at the center of the said connection member (18) which helps in operating the fan blades both for exhalation and inhalation of the air.

In an embodiment of the present invention, the said micro switch (28) is fixed at the edge of the exterior surface of the said frusto-conical tube either on the said forward edge (20, 20') or on the said rearward (22, 22') edge, depending upon the orientation of the fan blades.

Various other embodiments can be designed, by varying the position of the motor and the power source.

Figure 13:
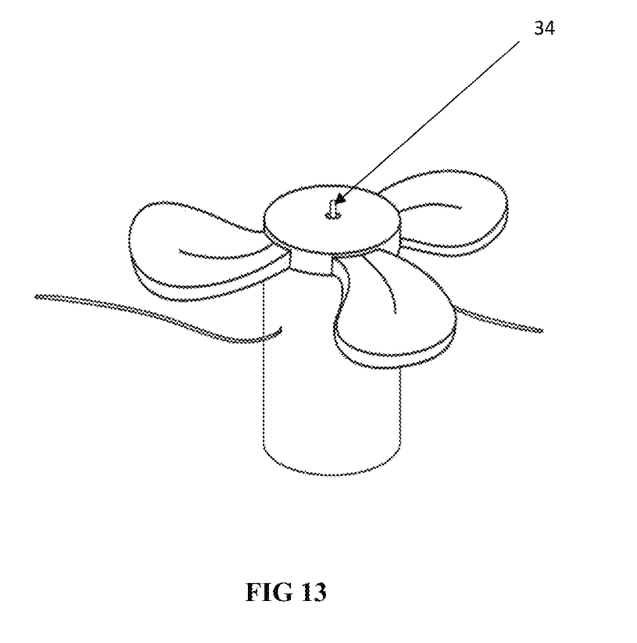
FIG. 13 illustrates the hub of the fan placed centrally in alignment with the central axis of the motor.

In another embodiment of the present invention, the said motor (14) can be accommodated within the hub (12) of the fan as in FIG. 13.

Figure 14:
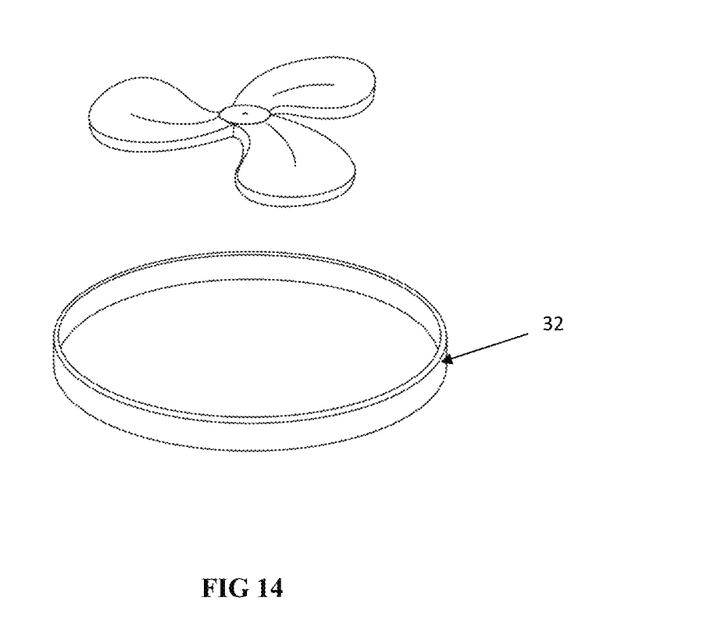
FIG. 14 illustrates a circular frame within which the hub of the fan along with the blades is to be placed.
Figure 15:
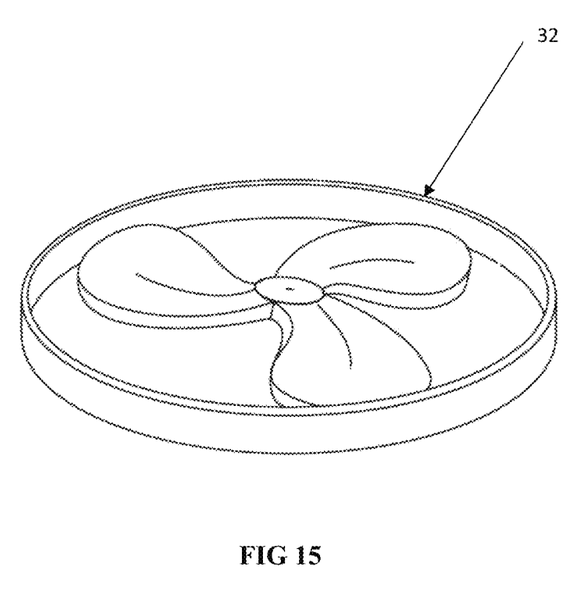
FIG. 15 illustrates the hub of the fan along with the blades placed within the circular frame.

In another embodiment of the present invention, the fan blades (10) are affixed at the central hub (12) of the fan, which comprises of means (not shown) for affixing the said fan hub (12), along the central axis (34) of the motor (14) as depicted in FIGS. 14-15.

In another embodiment of the present invention, the ventilating fan comprises a frame with a generally circular periphery containing the fan blades therein. Furthermore, in one end of the said frame a central space meant for housing an electric motor is accommodated.

The ventilating apparatus can further be modified by providing it with a filtering mechanism and also an inhalant with medication or with fragrance.

Figure 9:
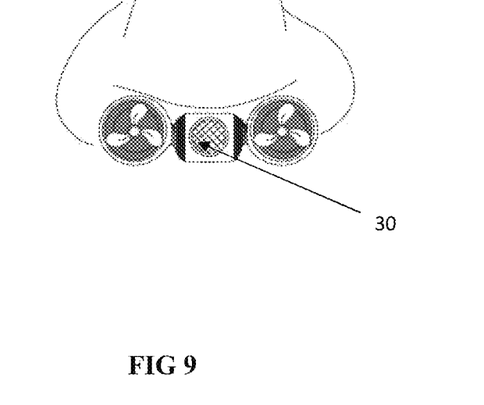
FIG. 9 illustrates the nasal ventilating device in both the nostrils with the connecting member accommodating an air filter or other dispenser such as medicine or air purifier alternatively the power source could be there or even solar cells

Therefore, in an embodiment of the present invention, to provide the nasal ventilating device with an inhalant having either fragrance or medication, a miniature container, adapted to rest between the pair of hollow conical frustum of the ventilating device of the present invention is designed. This container more particularly rests on the underside of the said connection member (18), which connects the said two hollow frusto-conical tubes (16, 16') housing with the said inhalation device as depicted in FIG. 9.

Figure 10:
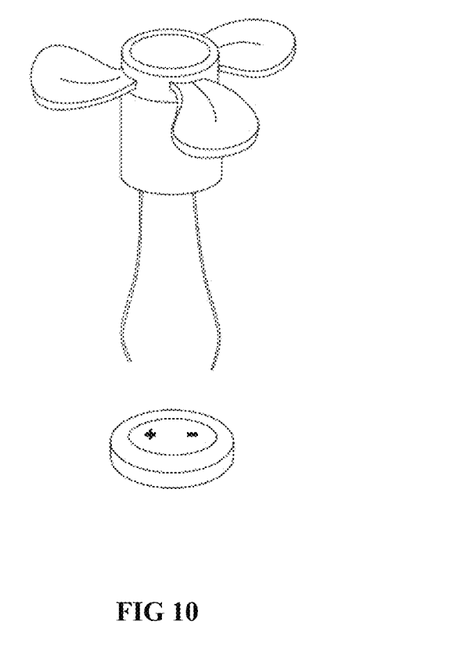
FIG. 10 illustrates the motor below the fan and connecting with the power source.

In another embodiment, the said connection member (18), connecting the said pair of hollow frusto-conical tubes (16, 16'), performs other additional functions, such as accommodating the said power button or a micro switch (28) for operating the ventilating fan as depicted in FIG. 10.

Figure 11:
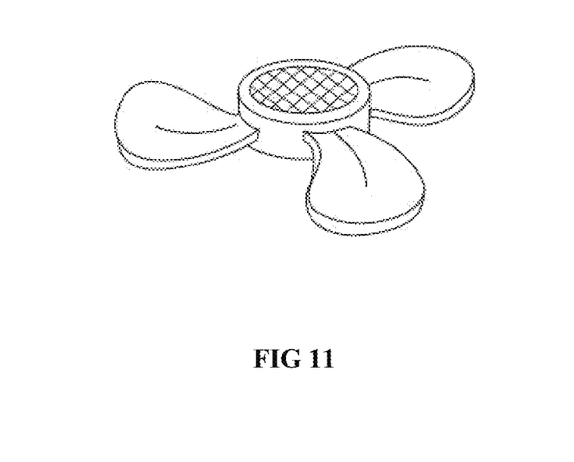
FIG. 11 illustrates the hub of the fan accommodating the motor in the center.

Referring to FIG. 11, the said connection member accommodates an air filter for filtering the air to be inhaled, thereby preventing inhalation of allergens as well as other pollutants present in the air.

Having now described the invention in detail as required by the patent statutes, those skilled in the art will recognize modifications and substitutions to the specific embodiments disclosed herein. Such modifications are within the scope and intent of the present invention as defined in the following claims.

The invention claimed is:

1. An air inhalation device, comprising:
    a pair of hollow frusto-conical tubes insertable into a pair of nostrils of a user, each tube of said pair of hollow frusto-conical tubes having an air passageway, and each tube of said pair of frusto-conical tubes tapering inward from a forward end to a rearward end;
    a vent fan;
    a motor connected to said vent fan; and
    a power source supplying power to said motor;
    a connection member joining said forward end of a first tube of said pair of frusto-conical tubes to said forward end of a second tube of said pair of frusto-conical tubes;
    a power switch to operate said vent fan, said power switch located on the connection member;
    wherein said rearward end of each tube of said pair of frusto-conical tubes is configured to be inserted into a nostril of said pair of nostrils with said connection remaining outside the pair of nostrils;
    wherein the vent fan is driven by the motor for enhancing the inhalation and exhalation of air.

2. An air inhalation device, of claim 1, wherein said vent fan includes a central hub and wherein said motor is accommodated within the central hub of said vent fan.

3. An air inhalation device, of claim 1, wherein said vent fan includes a central hub and wherein said motor is affixed just below the hub of said vent fan.

4. An air inhalation device of claim 1, wherein said connection member houses a container provided with a fragrant inhalant.

5. An air inhalation device for insertion within the nostrils, of claim 4, wherein said inhalant is a medicament.

* * * * *